(12) United States Patent
Leigh et al.

(10) Patent No.: US 9,031,662 B2
(45) Date of Patent: May 12, 2015

(54) IMPLANTABLE MEDICAL DEVICE INCLUDING SURFACE GEOMETRY HAVING REDUCED BIOFILM FORMATION CHARACTERISTICS

(75) Inventors: C. Roger Leigh, East Ryde (AU); Mark Von Huben, Waverton (AU)

(73) Assignee: Cochlear Limited, Macquarie University, NSW (AU)

( * ) Notice: Subject to any disclaimer, the term of this patent is extended or adjusted under 35 U.S.C. 154(b) by 468 days.

(21) Appl. No.: 13/145,304

(22) PCT Filed: Jan. 19, 2010

(86) PCT No.: PCT/AU2010/000042
§ 371 (c)(1),
(2), (4) Date: Jul. 19, 2011

(87) PCT Pub. No.: WO2010/081201
PCT Pub. Date: Jul. 22, 2010

(65) Prior Publication Data
US 2012/0022647 A1      Jan. 26, 2012

(51) Int. Cl.
*A61N 1/05*      (2006.01)
*A61N 1/375*    (2006.01)
*A61F 2/00*      (2006.01)
*A61N 1/32*      (2006.01)
*A61N 1/36*      (2006.01)
*H04R 25/00*    (2006.01)

(52) U.S. Cl.
CPC .............. *A61F 2/0077* (2013.01); *A61N 1/326* (2013.01); *A61N 1/36032* (2013.01); *A61N 1/375* (2013.01); *H04R 25/606* (2013.01); *H04R 2460/13* (2013.01); *H04R 25/65* (2013.01); *H04R 25/658* (2013.01)

(58) Field of Classification Search
USPC ........................................ 607/55–57, 36, 116
See application file for complete search history.

(56) References Cited

U.S. PATENT DOCUMENTS

| 5,462,644 | A | 10/1995 | Woodson |
| 8,412,304 | B2 * | 4/2013 | Kara et al. ................. 600/395 |
| 2004/0146715 | A1 * | 7/2004 | Guire et al. ................. 428/412 |
| 2005/0165464 | A1 | 7/2005 | Parker et al. |
| 2005/0177204 | A1 | 8/2005 | Zhang et al. |
| 2006/0020318 | A1 | 1/2006 | Lenarz et al. |
| 2006/0116743 | A1 * | 6/2006 | Gibson et al. ................. 607/57 |

FOREIGN PATENT DOCUMENTS

| WO | WO 03/088914 | 10/2003 |
| WO | WO 2006/007368 | 1/2006 |
| WO | WO 2008/051867 | 5/2008 |
| WO | 2008143889 A1 | 11/2008 |

OTHER PUBLICATIONS

Christensen et al. "Adherence of slime-producing strains of *Staphylococcus epidermidis* to smooth surfaces" Infect. Immun. 1982, 37(1):318.*

(Continued)

*Primary Examiner* — Brian T Gedeon

(57) ABSTRACT

An implantable medical device configured to be implanted in a recipient. The implantable medical device includes an implantable assembly, wherein the exterior geometry of the implantable assembly is adapted to inhibit formation of a biofilm thereon after implantation in the recipient.

17 Claims, 17 Drawing Sheets

(56) References Cited

OTHER PUBLICATIONS

International Search Report, Application No. PCT/AU2010/000042, mailed Feb. 17, 2010 (3 pages).
Written Opinion, International Application No. PCT/AU2010/000042, mailed Feb. 17, 2010 (4 pages).
International Preliminary Report on Patentability, Application No. PCT/AU2010/000042, mailed Jul. 19, 2011 (5 pages).
Georg Peters et al., "Adherence and Growth of Coagulase-Negative Staphylococci on Surfaces of Intravenous Catheters", The Journal of Infectious Diseases, vol. 146, No. 4, Oct. 1982, pp. 479-482.
Ernest D. Gray et al., "Effect of Extracellular Slime Substance From Staphylococcus Epidermidis on the Human Cellular Immune Response", The Lancet, Feb. 18, 1984, pp. 365-367.
George M. Johnson et al., "Interference with Granulocyte Function by Staphylococcus epidermidis Slime", Infection and Immunity, Cot. 1986, pp. 13-20.
S. S. Kaplan et al., "Biomaterial Associated Impairment of Local Neutrophil Function", Biomaterial Effects on Neutrophils, pp. M172-M175.
Hosmin Anwar et al., "Dynamic Interactions of Biofilms of Mucoid Pseudomonas aeruginosa with Tobramycin and Piperacillin", Antimicrobial Agents and Chemotherapy, vol. 36, No. 6, Jun. 1992, pp. 1208-1214.
William Costerton et al., "The application of biofilm science to the study and control of chronic bacterial infections", J. Clin. Invest. 112: 1466-1477 (2003).
D. Mack, "Molecular mechanisms of Staphylococcus epidermis biofilm formation", Journal of Hospital Infection (1999) 43 (Supplement): S113-S125.
Nickel et al., Antibiotic resistance of Pseudomonas aeruginosa colonising a urinary catheter in vitro., European Journal of Clinical Microbiology, 4:213-218 (1985).
Extended European Search Report in counterpart European Application No. 10730984.1, mailed Mar. 20, 2014, 9 pages.
Costerton, "The Biofilm Primer," Springer Series on Biofilms, 2007, pp. 5-7 and 56-61.
Jass, et al., "Medical Biofilms: Detection, Prevention and Control," Wiley, Chichester, 2003, p. 7.

* cited by examiner

IMPLANTABLE MEDICAL DEVICE INCLUDING SURFACE GEOMETRY HAVING REDUCED BIOFILM FORMATION CHARACTERISTICS

CROSS-REFERENCE TO RELATED APPLICATIONS

This application is a National Stage Application of International Application No. PCT/AU2010/000042, filed Jan. 19, 2010, and claims which claims priority from Australian Provisional Patent Application No. 2009900201 entitled "SURFACE MODIFICATION FOR IMPLANTABLE MEDICAL DEVICE", filed 19 Jan. 2009, which is hereby expressly incorporated by reference herein in its entirety.

BACKGROUND

1. Field of the Invention

The present invention relates generally to implantable medical devices, and more particularly, to an implantable medical device including surface geometry having reduced biofilm formation characteristics.

2. Related Art

One of the more common reasons to explant an implantable medical device (IMD) is the development of a chronic infection associated with the device after implantation into the recipient. This reason for explant has become of more importance in recent times due to the increased reliability of many types of IMDs. One infection source is thought to be the formation of biofilms on a surface region of an IMD. These biofilms occur when microbes colonize a surface and form a film or "slime" layer. This mode of microbe life is now considered more common than the more generally studied planktonic state of bacteria. Studies have shown that in the biofilm state, microbes or bacteria within the biofilm are protected by an extracellular matrix structure which also assists in nutrition. (See, e.g., Peters G et al., Adherence and growth of coagulate-negative staphylococci on surfaces of intravenous catheters. J Infect Dis 146:479-482 (1982); Gray E D et al, Effect of extracellular slime substance from *Staphylococcus epidermidis* on human cellular immune response. Lancet 18:365-367 (1984); Johnson G M et al, Interference with granulocyte function by *Staphylococcus epidermidis* slime. Infect Immun 54: 13-20 (1986); Kaplan S S et al, Biomaterial associated impairment of local neutrophil function. ASAIO Trans 36:M172-175 (1990); and Anwar H et al, Dynamic interactions of biofilms of mucoid *Pseudomonas aeruginosa* with tobramycin and piperacillin. Antimicrob Agents Chemother 36: 1208-1214 (1992).) In addition, microbes in the biofilm state express different genes than in the planktonic state. (See, e.g., Costerton J W et al., The Application of Biofilm Science to the Study and Control of Chronic Bacterial Infections, J Clin Invest 112: 1466-1477 (2003).) The process by which microbes form a biofilm on a surface region is now generally well accepted. The first step in this process is the attaching of free moving (planktonic) microbes to the relevant surface region. In subsequent steps, the attached microbes then colonize the surface and then develop into a mature biofilm. (See, e.g., Costerton J W, The Biofilm Primer (Springer Series on Biofilms), pp 5-7 (2007); and Mack D, Molecular mechanisms of *Staphylococcus epidermidis* biofilm formation. J Hosp Infect 43 SupphSl 13-125 (1999).)

The formation of a biofilm is thought to behave as a physical and/or chemical barrier to antimicrobial agents and the body's natural defenses against infection. Clinicians have observed that antibiotics have not been effective against infections resulting from biofilms despite assaying showing the component microbe of the biofilm to be of a type normally susceptible to antibiotics. (See, e.g., Costerton J W, The Biofilm Primer (Springer Series on Biofilms), pp 56-61 (2007).) Additionally, studies have shown that microbes in the biofilms state are up to a thousand times more resistant to antibiotics than in the planktonic state. (See, e.g., Jass, J., Surman, S., Walker, J. 'Medical Biofilms: Detection, Prevention and Control' Wiley, Chichester, p 7, (2003); Nickel et al, Antibiotic resistance of Pseudomonas aeruginosa colonising a urinary catheter in vitro., European Journal of Clinical Microbiology, 4:213-218 (1985).) Accordingly, should a biofilm form on a surface region of an IMD then it is more likely that this will result in a chronic infection, thereby resulting in the otherwise effective IMD having to be removed.

There have been a number of attempts to reduce the formation of biofilms on the surface regions of IMDs to reduce this instance of chronic infection. One approach involves the use of an electric field or current applied to the surface and surrounding regions to disrupt biofilm formation. This approach typically rquires a power supply to form the relevant electric field. This may necessitate the incorporation of a power supply into the IMD in the case where the IMD is passive, or alternatively placing an extra load requirement on an active powered IMD such as a cochlear implant or cardiostimulator device.

Other approaches to reducing the formation of biofilms on the surface regions of IMDs involve the use of enzymes or other antimicrobial agents as a coating on the relevant surface region of the IMD. However, the use of any antimicrobial agent or biocide may be susceptible to the adaptive abilities of any biofilm to develop a resistance to the therapeutic properties of the agent, thereby potentially rendering it not as effective as it otherwise might be. Furthermore, for IMDs which are intended for long term implantation, the effectiveness of these coatings may diminish over extended time periods. Additionally, the process of coating an IMD with a suitable antimicrobial agent or biocide also adds complexity and cost to the manufacture of IMDs as it generally involves the coating of unsuitable substrates such as silicone or may involve a high temperature process which the electronic components of an IMD cannot withstand.

SUMMARY

In an aspect the present invention, there is an implantable medical device configured to be implanted in a recipient, comprising an implantable assembly, wherein the exterior geometry of the implantable assembly is adapted to inhibit formation of a biofilm thereon after implantation in the recipient.

In another aspect of the present invention, there is an implantable medical device, comprising a shell hermetically enclosing a functional component of the implantable medical device, wherein at least some exterior inflection regions of the shell have at least one of an aspect ratio of about 2 or more, an angle of about 90 degrees or more, or a radius of curvature greater than about half a thickness of the implantable medical device, the thickness being located on the same plane on which the radius of curvature is located.

According to another aspect of the present invention, there is a method of manufacturing an implantable medical device, comprising identifying first geometries of first exterior surfaces of a first implantable medical device geometry having first biofilm formation characteristics, and identifying second geometries of second exterior surfaces of a second implantable medical device geometry having second biofilm formation characteristics, and forming at least some of the exterior surfaces of the implantable medical device to have the second identified geometries, wherein the second biofilm formation characteristics correspond to reduced biofilm formation relative to that of the first biofilm formation characteristics, and the first and second exterior surfaces are located at substantially corresponding locations, respectively, of the first and second implantable medical devices.

According to another aspect of the present invention, there is an implantable medical device configured to be implanted in a recipient, comprising an implantable assembly including surface means for inhibiting a formation of a biofilm thereon after implantation in the recipient.

BRIEF DESCRIPTION OF THE DRAWINGS

Illustrative embodiments of the present invention will be discussed with reference to the accompanying drawings wherein.

DETAILED DESCRIPTION

Figure 1:
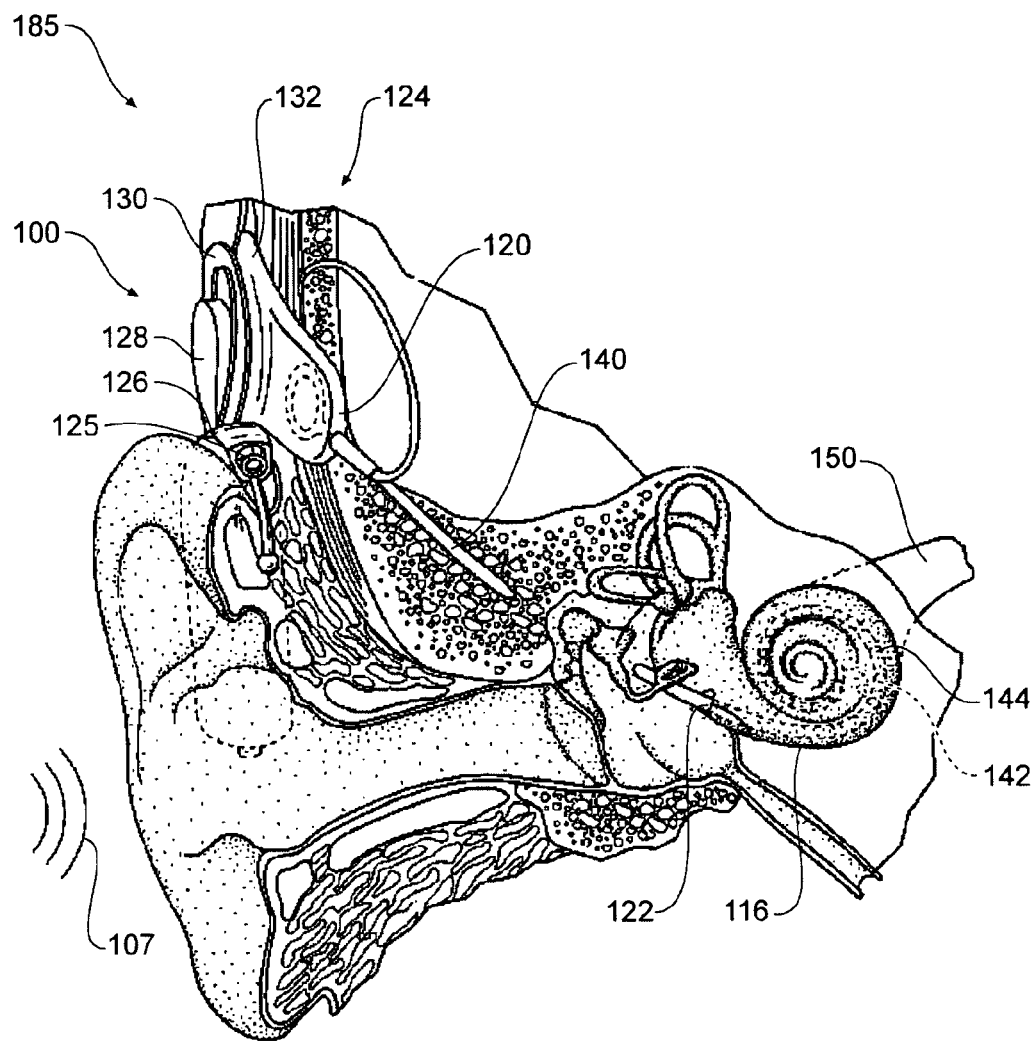
FIG. 1 depicts an exemplary cochlear implant system which may be advantageously adapted with embodiments of the present invention.

An embodiment of the present invention includes an implantable medical device configured to be implanted in a recipient. In an exemplary embodiment, the implantable medical device is part of a cochlear implant, and the following exemplary embodiment will be described as such. As detailed herein, other embodiments include other types of implantable medical devices.

The implantable medical device comprises an implantable assembly including a receiver and a stimulator of a cochlear implant. The exterior geometry of the implantable assembly is adapted to inhibit formation of a biofilm thereon after implantation in the recipient. In an exemplary embodiment, this is achieved through, for example, the use of surfaces of the implantable assembly having surface curvatures having higher radii of curvature than prior-art implantable medical devices, the use of depressions having width to depth ratios greater than prior-art implantable medical devices, and exterior angles that are greater than prior-art implantable medical devices.

In the following description, like reference characters designate like or corresponding parts throughout the several views of the drawings.

In some exemplary illustrative embodiments, the present invention will be described with reference to a cochlear implant system, this being an example IMD. In some embodiments, the present invention can be applied to other IMDs, such as, for example, IMDs that incorporate a surface region susceptible to the formation of a biofilm. These exemplary IMDs include, but are not limited to, devices such as implantable drug delivery systems, cardio-stimulator devices, orthopedic implants such as artificial joints, limbs and the like, dental implants, implantable sensors, stents and semi-permanent implantable medical devices such as catheters and intravenous delivery tubes, visual prosthesis, neuro-stimulators and other hearing prosthesis such as auditory brainstem implants, implantable hearing aids, direct acoustic cochlear stimulation (DACS) devices and bone anchored hearing aids.

Referring now to FIG. 1, cochlear implant system 185 comprises external component assembly 100 and internal (or implanted) component assembly 124. External assembly 100 comprises a behind the ear (BTE) speech processing unit or speech processor 126 connected to a transmission coil 130. Speech processor 126 includes an external microphone 125 for detecting sound and generating an electrical signal which is then processed by electronics within the speech processor 126 to generate coded signals. The coded signals are provided to an external transmitter unit 128, along with power from a power source such as a battery (not shown).

The internal component assembly or receiver/stimulator 124 includes a receiver unit 132 having an internal coil (not shown) that receives and transmits power and coded signals from external assembly 100 to a stimulator unit 120 to apply the coded signal along an electrode lead 140 to an electrode assembly 144 consisting of a plurality of electrodes 142 where each electrode consists of an electrode or stimulation contact and an electrode wire (not shown) which can be independently stimulated. Electrode assembly 144 is inserted into the cochlea 116 in an implantation procedure known as cochleostomy and in this example, the electrode assembly 144 is inserted into the scala tympani through an incision 122 in the wall of the cochlea with the electrodes 142 positioned to be substantially aligned with the basilar membrane portions of the cochlea 116 as described below.

The cochlea 116 is tonotopically mapped with different regions extending along the cochlea 116 being responsive to acoustic and/or stimulus signals in different frequency ranges. As one of ordinary skill in the art is aware, low frequency sounds stimulate the basilar membrane of the cochlea 116 most significantly at its apex, while higher frequencies more strongly stimulate the basilar membrane at the cochlea's base. To accommodate this property of the cochlea 116, the electrode assembly 144 is constructed and arranged to deliver suitable stimulating signals to individual basilar membrane portions of the cochlea 116 in accordance with the different frequency components of a received audio signal 107, thereby stimulating the auditory nerve 150. Thus, electrodes 142 of electrode assembly 144 located near the base of the cochlea are used to simulate high frequency sounds while electrodes 142 closer to the apex are used to simulate lower frequency sounds. It should be appreciated that although in FIG. 1 the electrodes 142 in electrode assembly 144 are arranged as a linear array other arrangements are possible.

Further details of the above and other exemplary cochlear implant systems in which embodiments of the present invention can be implemented include, but are not limited to, systems described in U.S. Pat. Nos. 4,532,930, 6,537,200, 6,565,503, 6,575,894 and 6,697,674, 5,758,651, WO 2005/122887.

Figure 2:
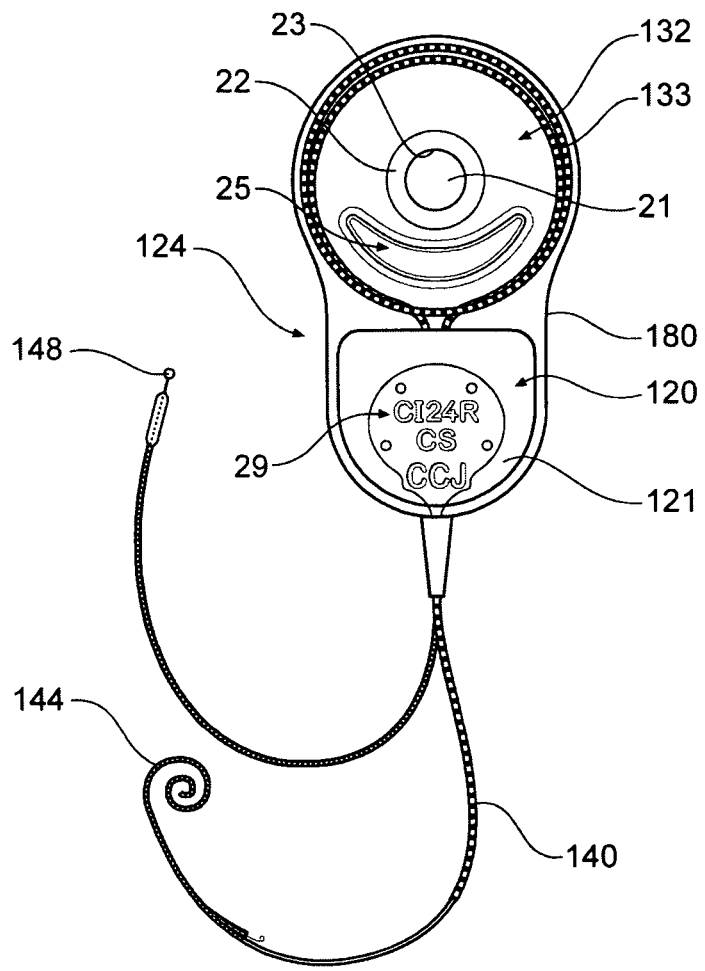
FIG. 2 is a front view of a receiver/stimulator similar to the internal component assembly of the cochlear implant system illustrated in FIG. 1.
Figure 3:
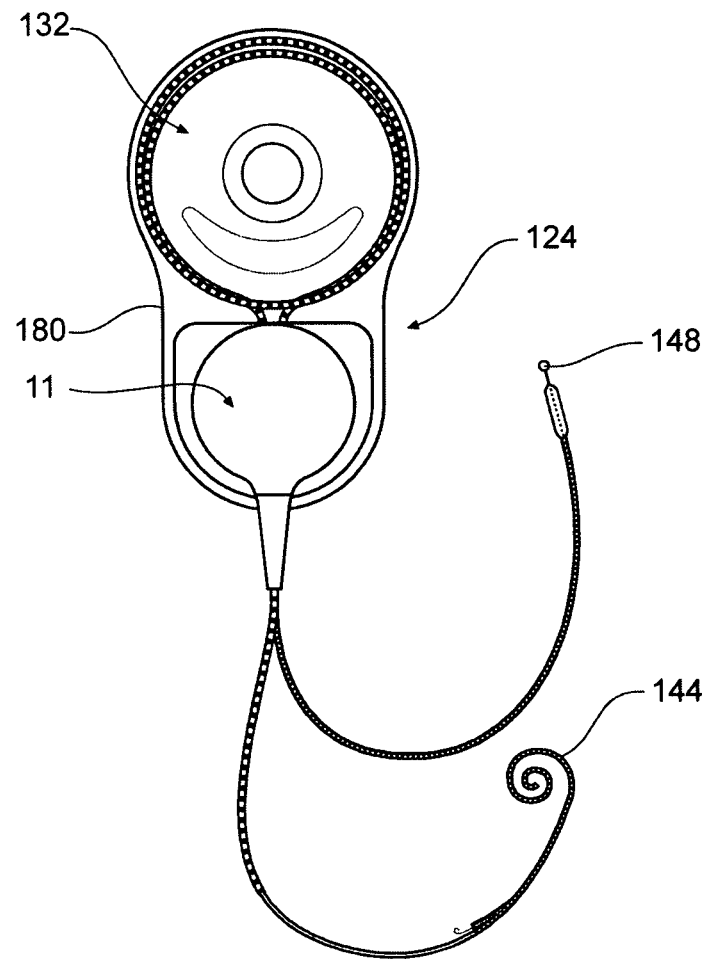
FIG. 3 is a rear view of the receiver/stimulator illustrated in FIG. 2.

Referring now to FIGS. 2 and 3, there are shown front and rear perspective views of a typical receiver/stimulator 124 as is known in the art (i.e., a cochlear implant developed and assembled by the assignee of the present application) which can form part of cochlear implant system 185 as illustrated in FIG. 1. Receiver/stimulator 124 is in the form of an implantable assembly, and is encapsulated or encased with a silicone shell 180 that hermetically seals the receiver unit 132 and stimulator unit 120. Receiver unit 132 is generally circularly shaped and incorporates a peripherally located internal antenna coil 133 sealed within silicone shell 180 and a centrally located attachment magnet 21 which is received within a pocket 22 having a circular aperture 23 formed in silicone shell 180 which forms an interface region between the surface of magnet 21 and pocket 22. An arcuate depression or channel 25 is formed in the shell 180 of the receiver unit 132 which functions to provide added flexibility to the receiver unit 132 portion of the receiver/stimulator 124 so that it may be wrapped about the skull on implantation.

Stimulator unit 120 incorporates the processing electronics for processing the signal received from receiver unit 132 housed within rigid body or case 121 typically formed of titanium or other biocompatible material and extracochlear electrode (ECE) plate 29 which is typically hermetically welded to case 121. Extending from stimulator unit 120 is an electrode lead 140 terminating in an electrode assembly 144, and a reference electrode 148. Reference electrode 148 and ECE plate 29 both provide a return pathway for current applied at the electrodes 142 of electrode assembly 144 in the commonly used stimulation mode. Located underneath or on the skull side of stimulator unit 120 there is located a pedestal 11 for recessing in the bone of the recipient on implantation (as seen in FIG. 3).

Receiver/stimulator unit 124 includes a number of surface regions that are potentially susceptible to the formation of a biofilm including, but not limited to, the receiver/stimulator shell 180, depression or channel 25 located in receiver unit 132, the pedestal region 11 which in this exemplary embodiment is located underneath stimulator unit 120, the exposed surface of magnet 21, the interface region between the circular aperture of 23 of the silicone pocket 22, the top or "skin" surface of stimulator unit 120, the junction region between the leads 140 and 148 and the case 121, and any embossed lettering or other surface feature that may be formed on the ECE plate 29 or any other exposed surface of stimulator unit 120 such as depicted in FIG. 2.

Referring now to FIGS. 4 to 9, there is shown a number of illustrative embodiments of a receiver/stimulator or more generally an IMD that is adapted to reduce or inhibit the formation of a biofilm on a surface region of the device in accordance with an exemplary embodiment of the present invention. The term surface configuration is taken throughout the specification to relate to the geometrical properties of a surface region such as surface curvature and/or smoothness and/or feature dimensions.

Figure 4:
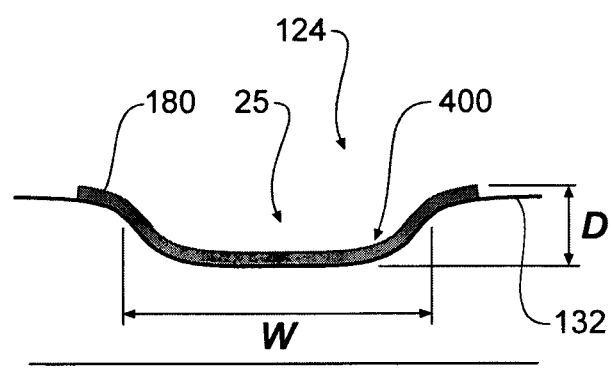
FIG. 4 is a figurative view of a first surface region of a receiver/stimulator adapted in accordance with an illustrative embodiment of the present invention.

Referring now to FIG. 4, there is shown a surface region 400 of a receiver/stimulator 124 whose surface form configuration has been adapted in accordance with an exemplary embodiment of the present invention. In this illustrative embodiment, the surface form configuration of the surface region 400 corresponding to channel 25 located on shell 180 is adapted to maximize the aspect ratio, defined as the ratio of the width W to the depth D of channel 25, that is possible within the constraints of the size and shape of the receiver unit 132, with a lower bound for the aspect ratio of 2. This can be contrasted with the aspect ratio of the channel 25 of the prior art device depicted in FIGS. 2 and 3 where the aspect ratio reduces below 2 at the corners of channel 25. Thus, an exemplary embodiment includes an exterior of an implantable assembly that includes an arcuate depression configured to provided longitudinal flexibility to the implantable assembly relative to the depression thereby permitting the implantable assembly to flex about a contour of a skull of the recipient, wherein a ratio of the width to depth of the arcuate depression is 2 or more at all locations of the arcuate depression.

Figure 5:
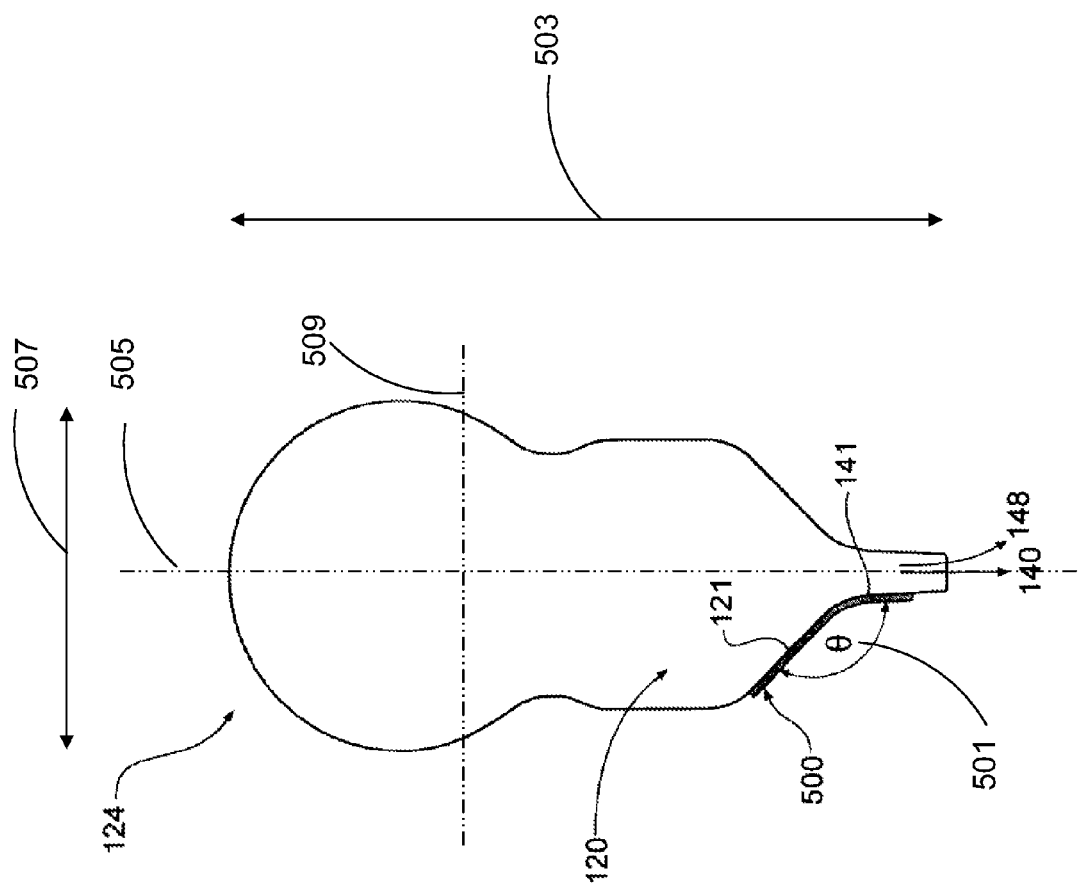
FIG. 5 is a figurative view of a second surface region of a receiver/stimulator adapted in accordance with an illustrative embodiment of the present invention.

Referring now to FIG. 5, there is shown a surface region 500 of a receiver/stimulator 124 whose surface configuration has been adapted in accordance with an exemplary embodiment of the present invention. In this illustrative embodiment, the surface configuration of the surface region 500 is located where the electrode lead 140 and reference electrode 148 are connected to the stimulator unit 120 of receiver/stimulator 124. In this embodiment, the angle θ (reference number 501) defined between the edge portion 121 of stimulator unit 120 and the connecting portion 141 of electrode lead 140 is adapted to be greater than 135 degrees. In some embodiments, where possible, angles of a surface region may be maximized within the constraints of the size and shape of the device, with a lower bound of not less than 90 degrees. In an exemplary embodiment, this may eliminate edges or sharp depressions in the surface region. As may be seen in FIG. 5, an exemplary embodiment of the present invention includes an implantable assembly that has an exterior length 503 extending along a longitudinal axis 505 of the implantable medical device, an exterior width 507 extending along a first lateral axis 509 and, with reference to FIG. 7, an exterior thickness 711 extending along a second lateral axis 713 (not shown in FIG. 5, but extending out of the page of FIG. 5). The second lateral axis 713 is normal to the first lateral axis 509, and both the first lateral axis 509 and the second lateral axis 713 are normal to the longitudinal axis 505. In an exemplary embodiment, the exterior thickness 711 is smaller than the exterior width 507, and both are smaller than the exterior length 503. As may be seen from FIG. 5, the implantable assembly includes an outer profile that, when viewed along the second lateral axis 713 has no angles less than 90 degrees. In an exemplary embodiment, the implantable assembly includes an outer profile that, when viewed along the second lateral axis 713, has no angles less than 135 degrees.

Figure 6:
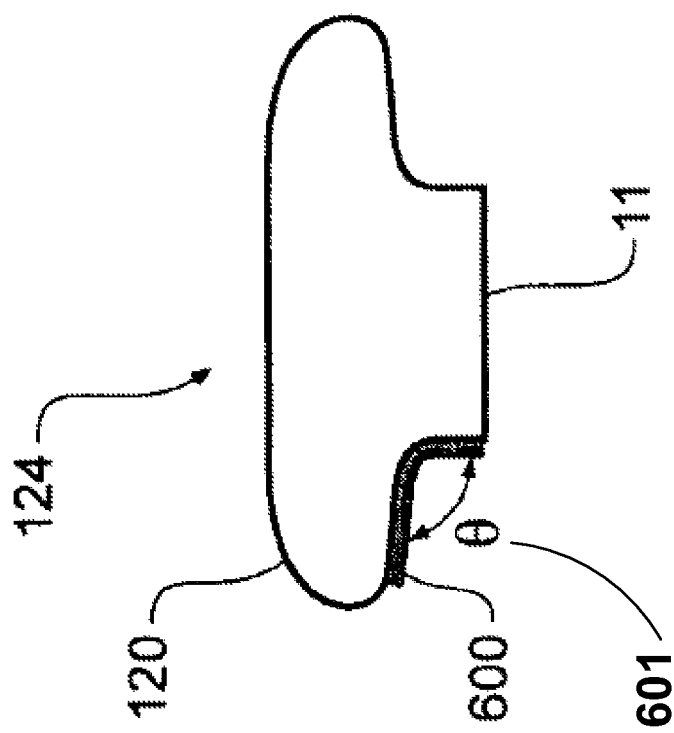
FIG. 6 is a figurative view of a third surface region of a receiver/stimulator adapted in accordance with an illustrative embodiment of the present invention.

Referring now to FIG. 6, there is shown a surface region 600 of a receiver/stimulator 124 whose surface configuration has been adapted in accordance with an exemplary embodiment of the present invention. In this illustrative embodiment, the surface region 600 corresponds to where pedestal 11 is attached or joined to receiver/stimulator unit 124. In this exemplary embodiment, the angle θ (identified as reference number 601) formed by the side wall of pedestal 11 with respect to the receiver/stimulator unit 124 is not less than 90 degrees.

Figure 7:
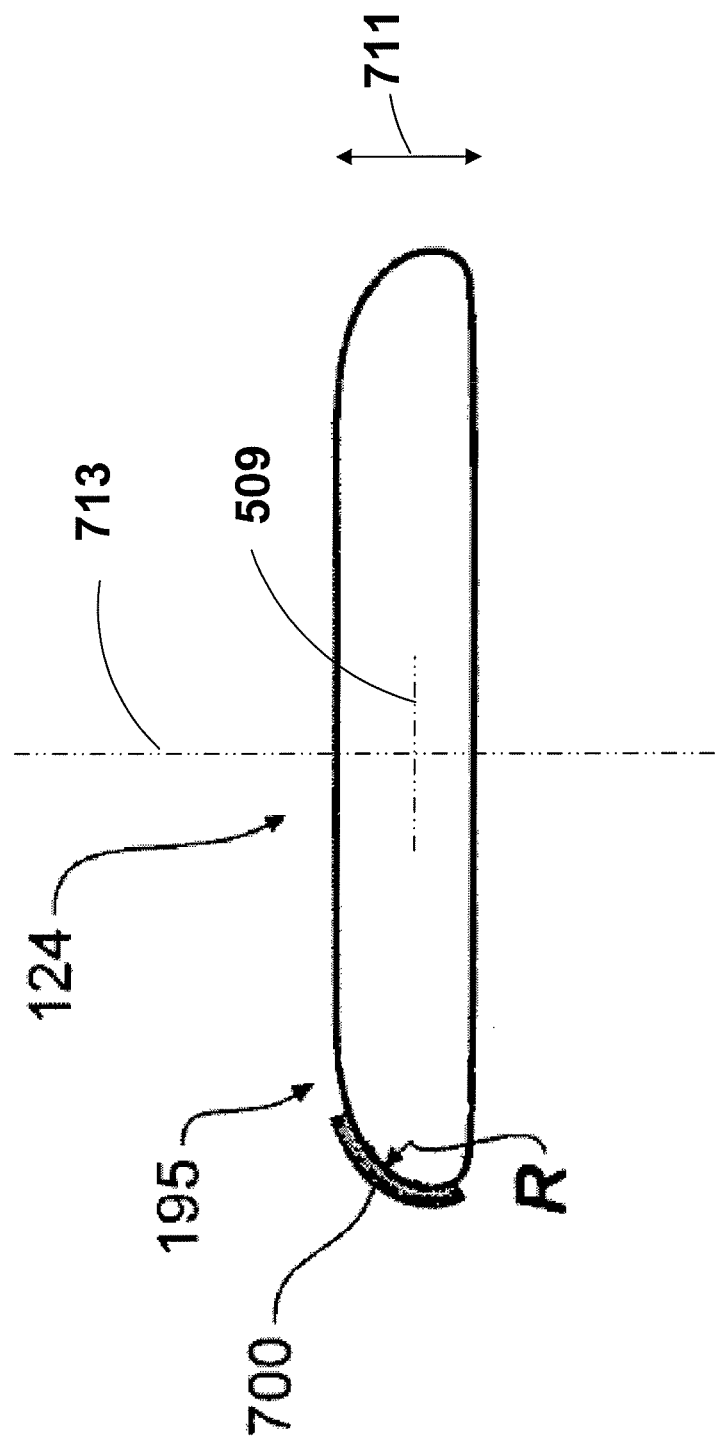
FIG. 7 is a figurative view of a fourth surface region of a receiver/stimulator adapted in accordance with an illustrative embodiment of the present invention.

Referring now to FIG. 7, there is shown a surface region 700 of a receiver/stimulator 124 whose surface form configuration has been adapted in accordance with an exemplary embodiment of the present invention. In this exemplary embodiment, the surface region 700 corresponds to the skin side 195/side not facing the recipient's bone of the receiver/stimulator unit 124 where the external radii R is greater than half the thickness 711 of the device at that point. This provides that those regions which are more likely to be in microbial contact, such as skin side/side not facing the recipient's bone of receiver/stimulator unit 124 will have an appropriate surface configuration. Accordingly, in an exemplary embodiment of the present invention, there is an implantable assembly that has an exterior length 503 extending along a longitudinal axis 505 of the implantable medical device, an exterior width 507 extending along a first lateral axis 509 and exterior thickness 711 extending along a second lateral axis 713 normal to the first lateral axis 509. In this exemplary embodiment, both the first lateral axis 509 and the second lateral axis 713 are normal to the longitudinal axis 505. The exterior thickness 711 is smaller than the exterior width 507. In this exemplary embodiment, the transitional regions extending from an outer profile of the implantable assembly, when viewed along the longitudinal axis, to a top side of the implantable assembly have an external radius of curvature greater than half the thickness 711 of the implantable medical device. In an exemplary embodiment, the thickness 711 lies on the same plane on which the external radius of curvature lies. In an exemplary embodiment the implantable medical device is constructed and arranged to be implanted in the recipient such that the top side of the implantable assembly faces away from the skull of the recipient.

As detailed above, the embodiment depicted in FIG. 7 addresses a radius of curvature on a side of the implantable medical device facing away from the bone of the recipient. It has been found that in some embodiments, the environment sides of the implantable medical device facing away from the bone of the recipient and/or in contact with the bone of the recipient is more conducive to biofilm formation/microbial infection than that on the side facing the bone/in contact with the bone. In some embodiments, this difference is significant enough that some of the inventive features as detailed herein are only applied side facing away from the bone/not in contact with the bone. However, in other embodiments, the inventive features are applied to other sides as well. Also, some implantable medical devices are implanted in such a manner that no side faces, or at least touches, bone. Thus, the inventive features may be applied to all sides in some embodiments.

In accordance with another illustrative exemplary embodiment of the present invention, outer surfaces of the receiver/stimulator such as the silicone shell 180 or the surface of magnet 21 are adapted to have a surface smoothness smoother than about 0.4 μm Ra. Magnet 21 may be encased in a biocompatible shell or casing formed of titanium or other biocompatible material which comes in two parts with the lower part forming a container for the magnetic material and the upper part forming a lid which is hermetically welded to the lower part. For a magnet 21 of this configuration, the outer surface of the casing is polished to obtain the desired surface smoothness as specified above. For the silicone shell, the smoothness is obtained by providing corresponding silicone molds that are polished to be smoother than 0.05 μm Ra.

In the embodiments described above, the surface form configuration is adapted to reduce, including inhibit, the formation of a biofilm on a surface region of an implantable medical device. In these exemplary illustrative embodiments, the surface form configuration has been modified or adapted to inhibit or reduce the attachment of microbes or bacteria to the surface region by enhancing the ability of body fluids to flow with respect to the surface region, principally by reducing the overall surface curvature of a region or by increasing its smoothness. As microbial attachment to the surface is the first step in biofilm formation, the reduction of this microbial attachment will function to prevent or reduce biofilm formation.

As would be appreciated by those skilled in the art, other adaptations to the surface form configuration which function to reduce, including inhibit, the formation of a biofilm are also contemplated to be within the scope of the invention. As has been discussed, the formation of a biofilm on a surface region represents a significant and difficult to treat infection source for implantable medical devices such as cochlear implants.

Figure 8:
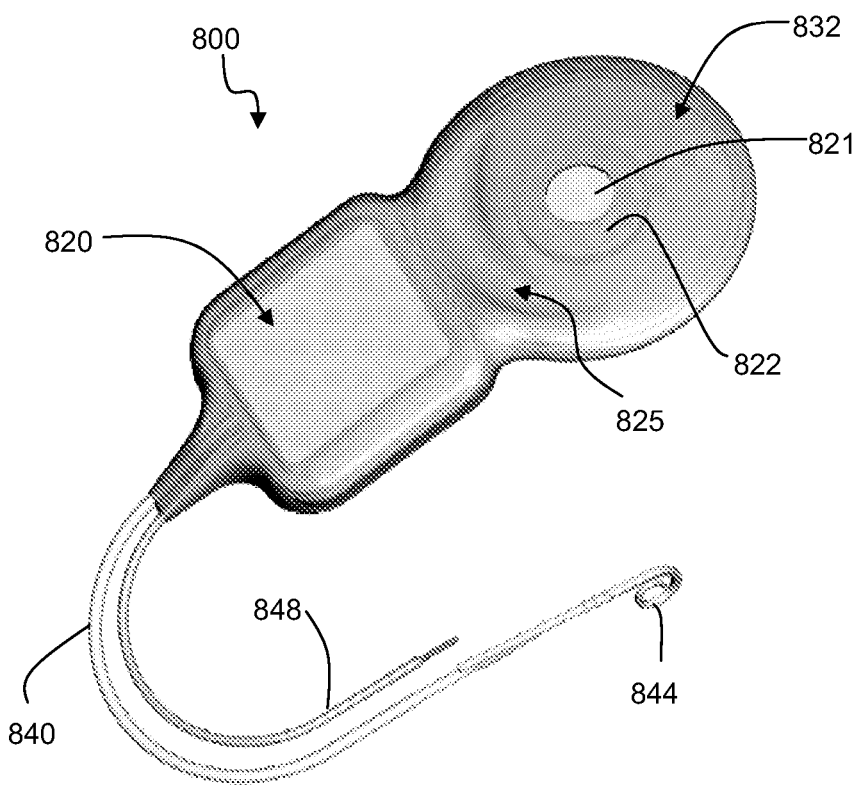
FIG. 8 is a front perspective view of a receiver/stimulator embodying a number of surface regions adapted in accordance with illustrative embodiments of the present invention.
Figure 9:
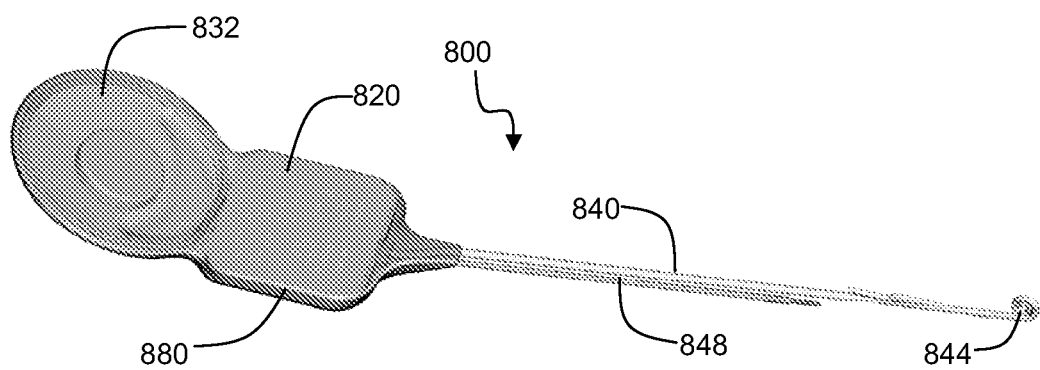
FIG. 9 is a rear side view of the receiver/stimulator illustrated in FIG. 8.

Referring now to FIGS. 8 and 9, there is shown front and rear perspective views of a receiver/stimulator 800 incorporating a number of surface regions adapted in accordance with illustrative embodiments of the present invention. FIGS. 8 and 9 depict an exemplary embodiment of an implantable medical device configured to be implanted in a recipient, comprising an implantable assembly, wherein the exterior geometry of the implantable assembly is adapted to inhibit formation of a biofilm thereon after implantation in the recipient.

In an exemplary embodiment of the present invention, some, a majority of, or substantially all, exterior inflection regions (e.g., the depression or channel 25, the outer contours depicted in FIGS. 5, 6 and/or 7, etc.) of the implantable assembly have at least one of an aspect ratio of about 2 or more, an angle of about 90 degrees or more, or a radius of curvature greater than about half a thickness of the implantable medical device. In an exemplary embodiment of the present invention, some, a majority of, or substantially all non-receptacle exterior inflection regions (e.g., the depression or channel 25, but not the aperture 823/pocket 822, which receives the magnet and not the orifice through which the electrode leads 840 extend) of the implantable medical device have at least one of an aspect ratio of 2 or more, an angle of 90 degrees or more, or a radius of curvature greater than half the thickness of the implantable medical device.

As with receiver/stimulator 124 depicted in FIGS. 2 and 3, receiver/stimulator 800 includes a receiver unit 832 and a stimulator unit 820, with an electrode lead 840 terminating in an electrode assembly 844 and a reference electrode 848 extending from the body of stimulator unit 820. As with receiver/stimulator 124, receiver/stimulator 800 is encased or encapsulated within a silicone shell 880 except for ECE plate region.

In order to assess the effectiveness of the modification of the surface form configuration in the reducing the propensity for, or the likelihood of, formation of a biofilm, an experiment was conducted comparing the rate of bacteria formation and adhesion on a first receiver/stimulator 124 as depicted in FIGS. 2 and 3 to the rate of bacteria formation and adhesion on a second receiver/stimulator 800 such as depicted in FIGS. 8 and 9. As discussed above, receiver/stimulator 800 incorporates a number of surface regions whose surface form configuration has been adapted in accordance with an exemplary embodiment of the present invention.

In the experiment, the biofilm development and attachment sites were compared between two receiver/stimulators 800 and two receiver/stimulators 124 by measuring the response of surface regions to exposure to a *Staphylococcus aureus* broth culture based on the *Staphylococcus aureus* strain CI494 which was isolated from an infected cochlear device obtained from St Vincent's Hospital, Melbourne, Australia.

In summary, the experimental procedure involved both receiver/stimulators 800, 124 being individually suspended in a broth of a known biofilm forming strain of *Staphylococcus aureus* for a predetermined period. The devices were then removed and placed in a stain known to cause the microbes to fluoresce. The devices were then rinsed to remove unattached microbes and viewed under a suitable florescent microscope to identify the position of attached microbes.

In detail, each of the pair of receiver/stimulators 800, 124 was treated in accordance with the following experimental protocol:
1. All of the four devices were coated with Foetal Calf Serum (FCS) to provide a conditioning film at 4° C. for 24 hours.
2. The devices were then removed from coating jars, washed with sterile H2O and mounted individually for broth incubation.
3. The devices were then suspended in 400 mL Tryptic Soy Broth and inoculated with 1:10,000 dilution of overnight culture of *Staphylococcus aureus*. The suspended devices were placed on a multi-point magnetic stirrer plate at 37° C. with each device's own magnet providing gentle stirring.
4. The devices were then incubated for 48 hours with a media change at 24 hours.
5. The devices were then removed from the broth culture and washed in 3 changes of sterile phosphate buffered saline (PBS) with rapid stirring to remove loosely adherent bacteria.
6. The devices were then stained with 1:2000 dilution of Syto9 (Molecular Probes) in sterile PBS.
7. The devices were then washed again in sterile PBS with stirring.
8. The devices were then viewed using an inverted microscope with epifluorescent capability (Olympus 1×71).
9. The device leads were then removed at their junction with the stimulator and devices placed in sterile PBS.
10. Devices were then sonicated to remove adherent bacteria.
11. Bacterial numbers attached to devices determined by colony forming units (CFU) counting.

Figure 10:
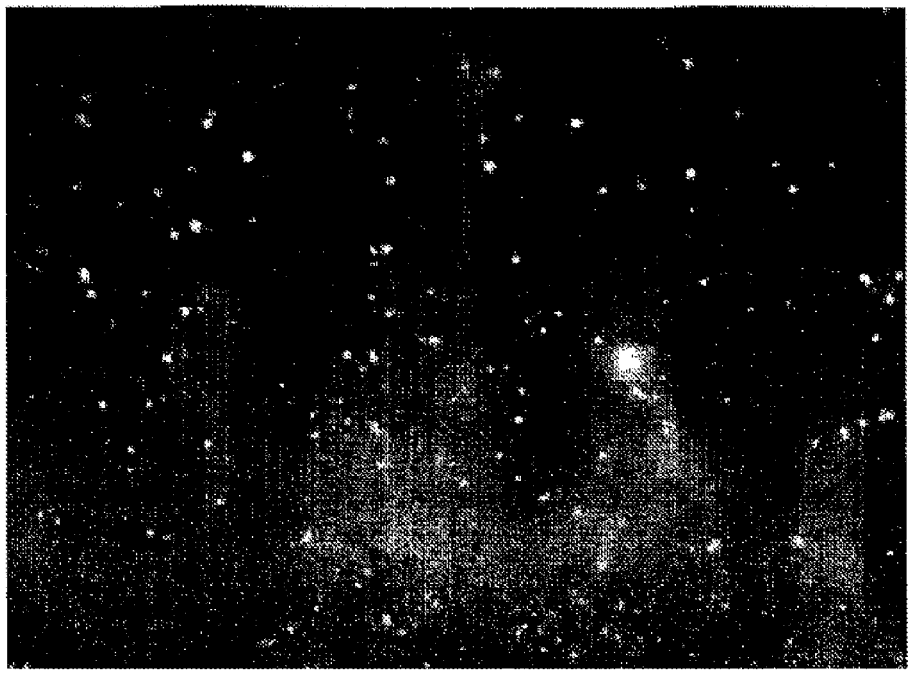
FIG. 10 is a fluorescent image taken at 200× magnification of a receiver/stimulator of the type illustrated in FIGS. 2 and 3 depicting bacteria attached to the surface of the magnet.
Figure 11:
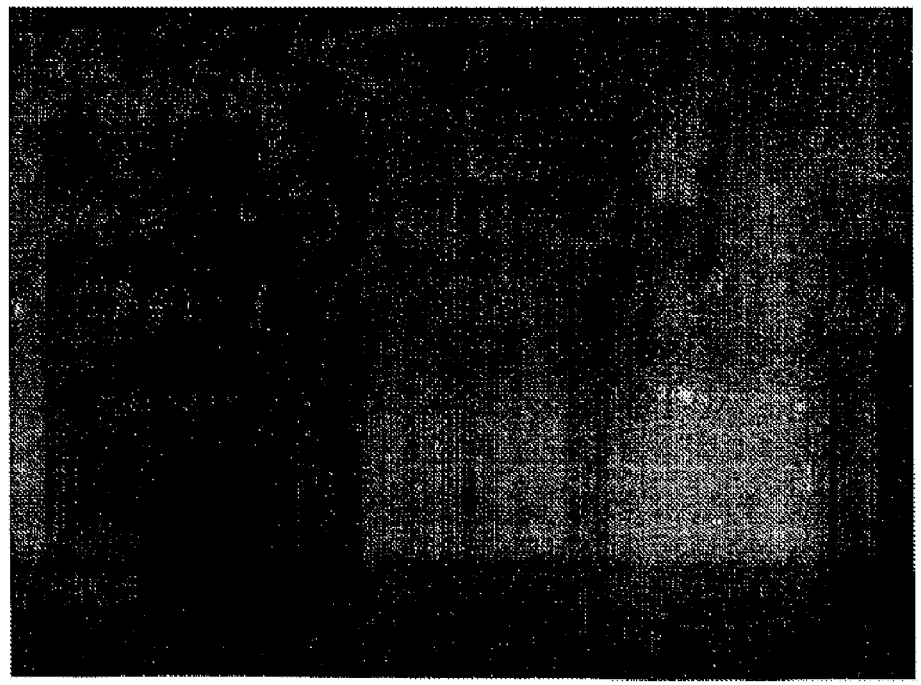
FIG. 11 is a fluorescent image taken at 200× magnification of a receiver/stimulator of the type illustrated in FIGS. 8 and 9 depicting bacteria attached to the surface of the magnet.
Figure 12:
FIG. 12 is a fluorescent image taken at 200× magnification of a receiver/stimulator of the type illustrated in FIGS. 2 and 3 depicting bacteria attached at the interface region between the interior circular edge of the silicone pocket and the magnet.
Figure 13:
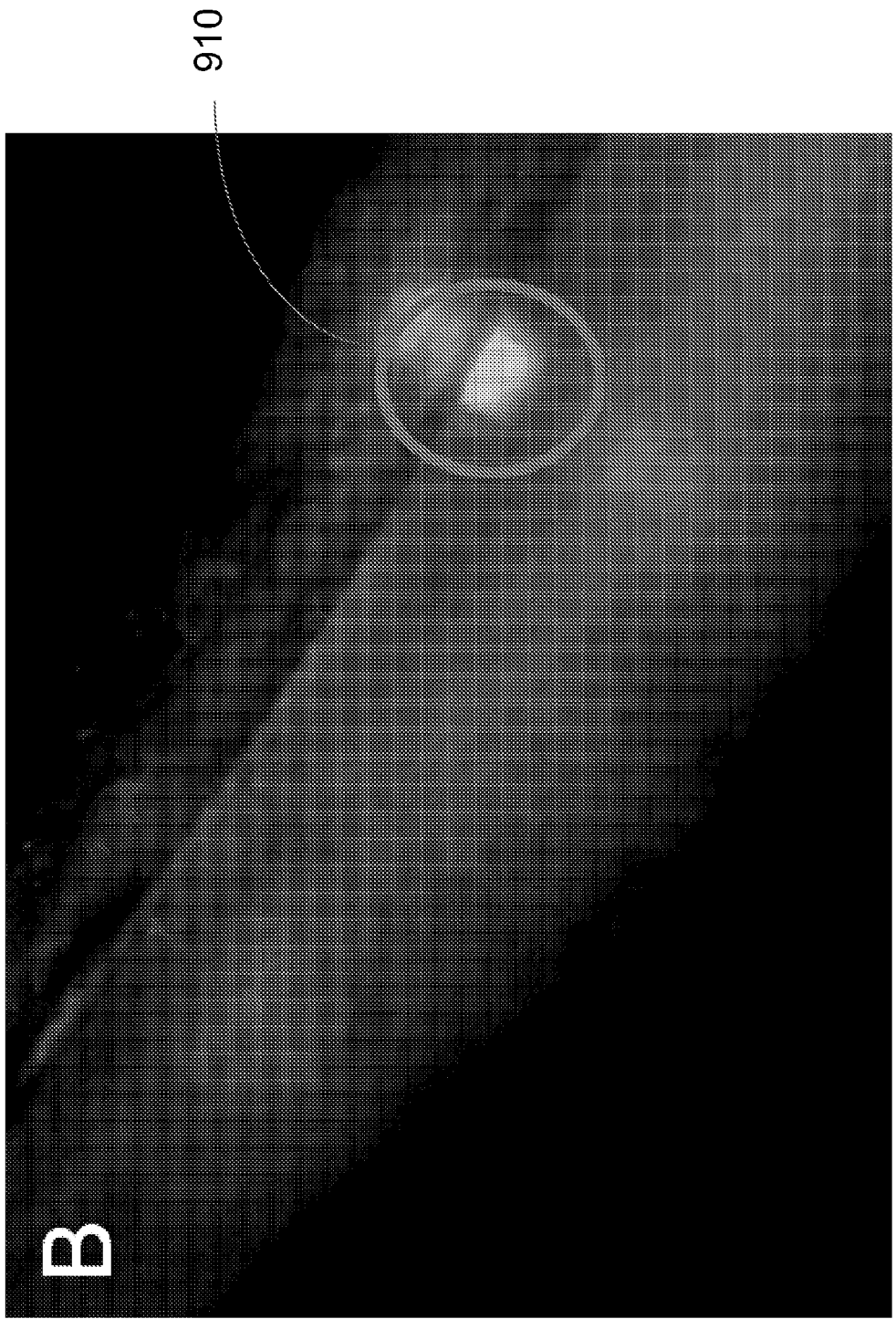
FIG. 13 is a fluorescent image taken at 200× magnification of another receiver/stimulator of the type illustrated in FIGS. 2 and 3 depicting the same interface region as depicted in FIG. 12.

Referring now to FIGS. 10 and 11, there are shown fluorescent images taken at 200× magnification comparing the amount of attached bacteria on the surface of the magnet 21, 821 for receiver/stimulator 124 (FIG. 10) where the surface smoothness of the magnet casing is greater than 0.4 µm Ra and receiver/stimulator 800 (FIG. 11) where the surface smoothness is less than 0.4 µm Ra. As can be readily observed, the surface of magnet 821 of receiver/stimulator 800 has less attached bacteria than the surface of the magnet 21 of receiver/stimulator 124.

Referring now to FIGS. 12 to 15, there are shown fluorescent images taken at 200× magnification comparing the amount of attached bacteria at the interface region defined by the edge of the circular aperture 23, 823 of the silicone pocket 22, 822 and the magnet 21, 821 for receiver/stimulator 124 (see FIGS. 12 and 13) and receiver/stimulator 800 (see FIGS. 14 and 15) respectively. The interface region of receiver/stimulator 124 shows moderate bacterial attachment 900 (see FIG. 12) with evidence of some microcolony formation 910 on the rough portions of the edge of the circular aperture 23 of silicone pocket 22 (see FIG. 13). In comparison, the corresponding smoother edges of receiver/stimulator 800 have almost no attached bacteria in the two devices tested (see FIGS. 14 and 15).

Figure 14:
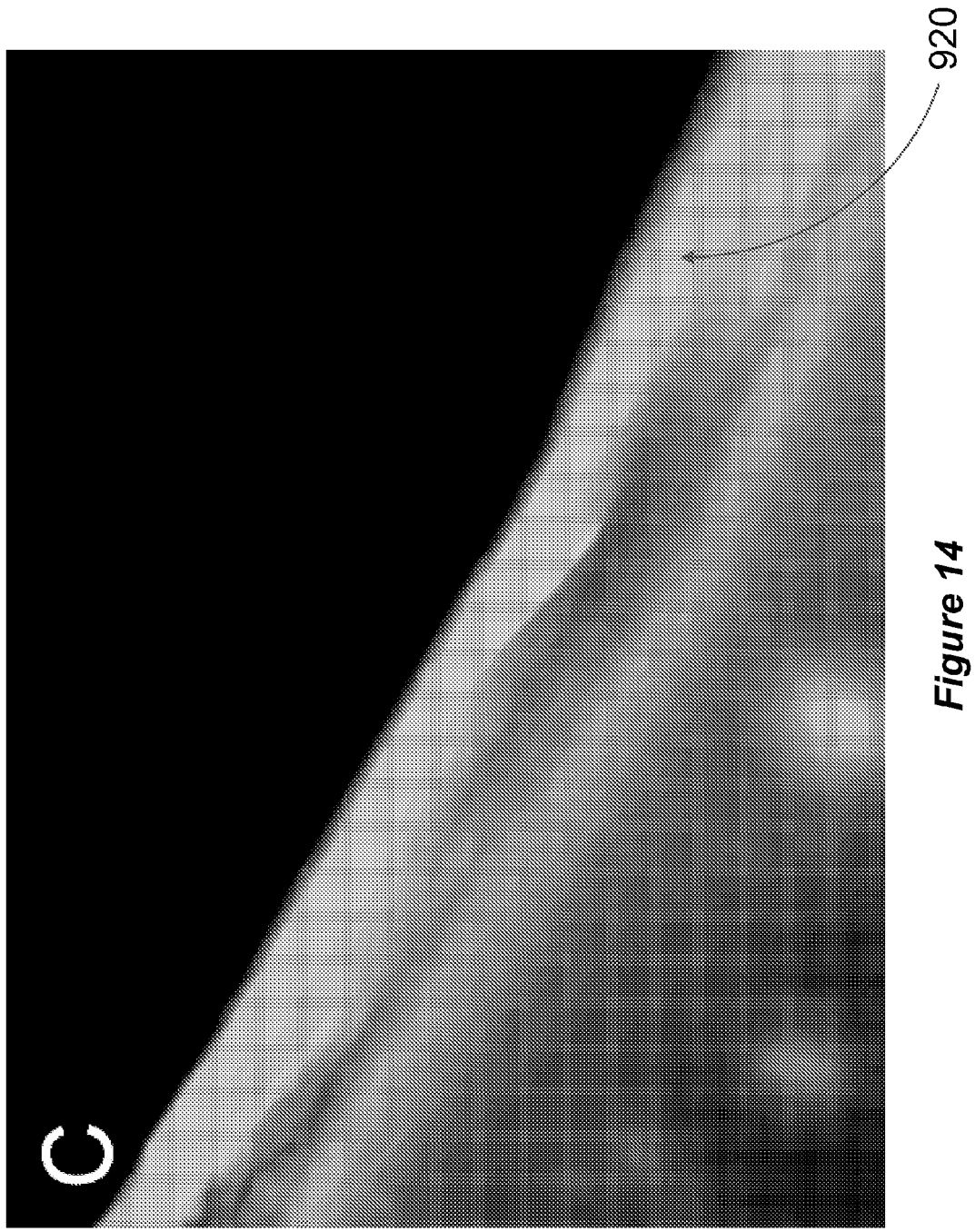
FIG. 14 is a fluorescent image taken at 200× magnification of a receiver/stimulator of the type illustrated in FIGS. 8 and 9 depicting bacteria attached at the same interface region as depicted in FIG. 12.
Figure 15:
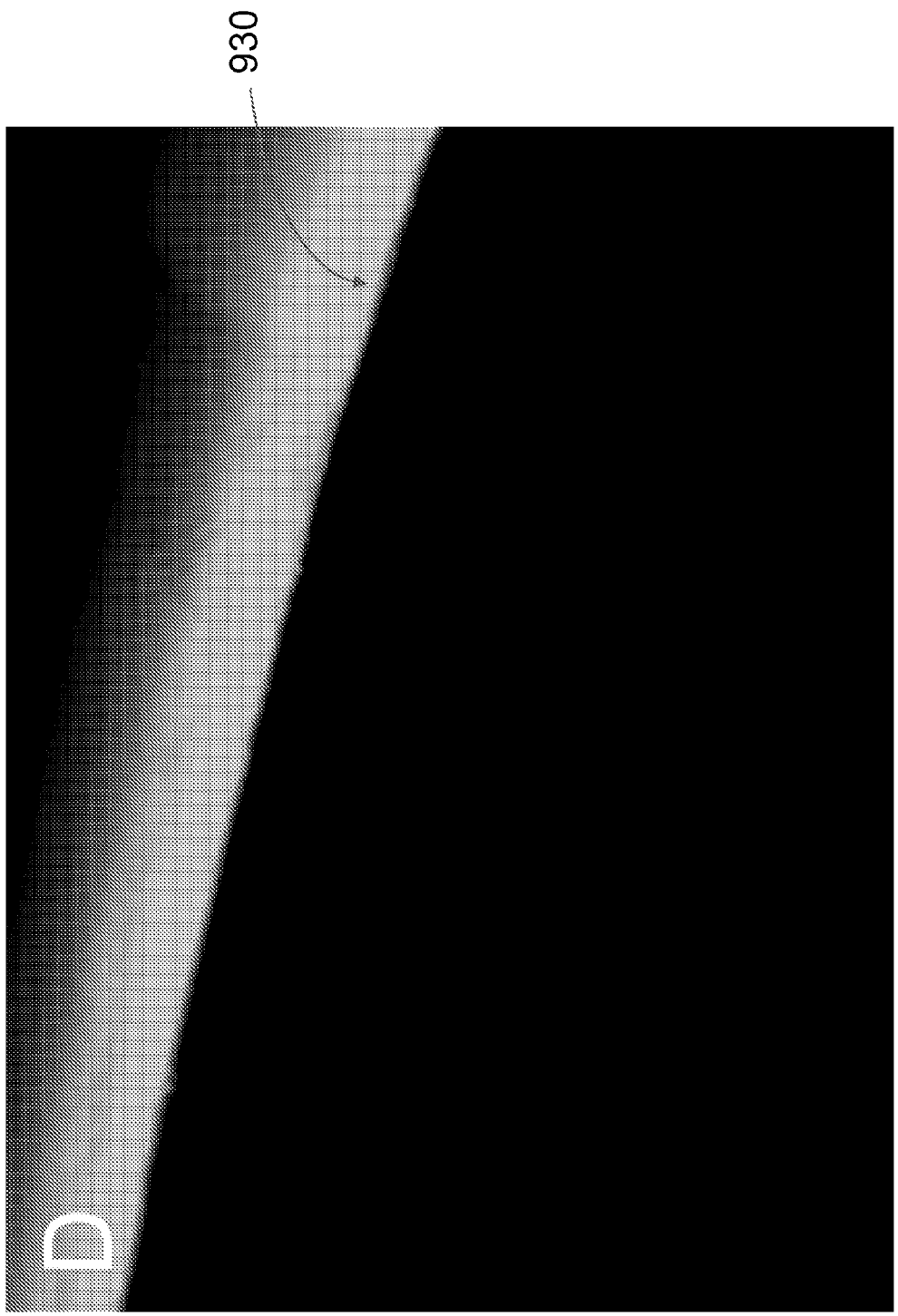
FIG. 15 is a fluorescent image taken at 200× magnification of another receiver/stimulator of the type illustrated in FIGS. 8 and 9 again depicting bacteria attached at the same interface region as depicted in FIG. 12.
Figure 16:
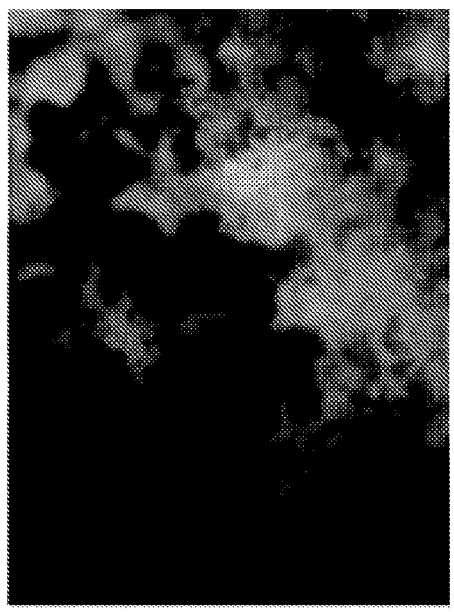
FIGS. 16A & 16B are fluorescent images taken at 200× magnification of receiver/stimulators of the type illustrated in FIGS. 2 and 3 depicting bacteria attached in the region of the arcuate channel in the receiver unit.
Figure 16:
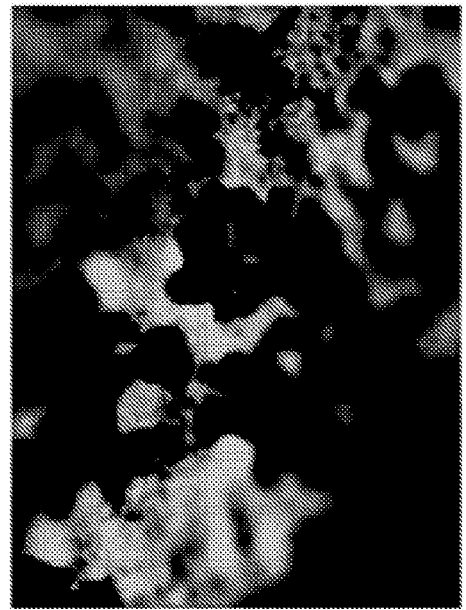
Figure 17:
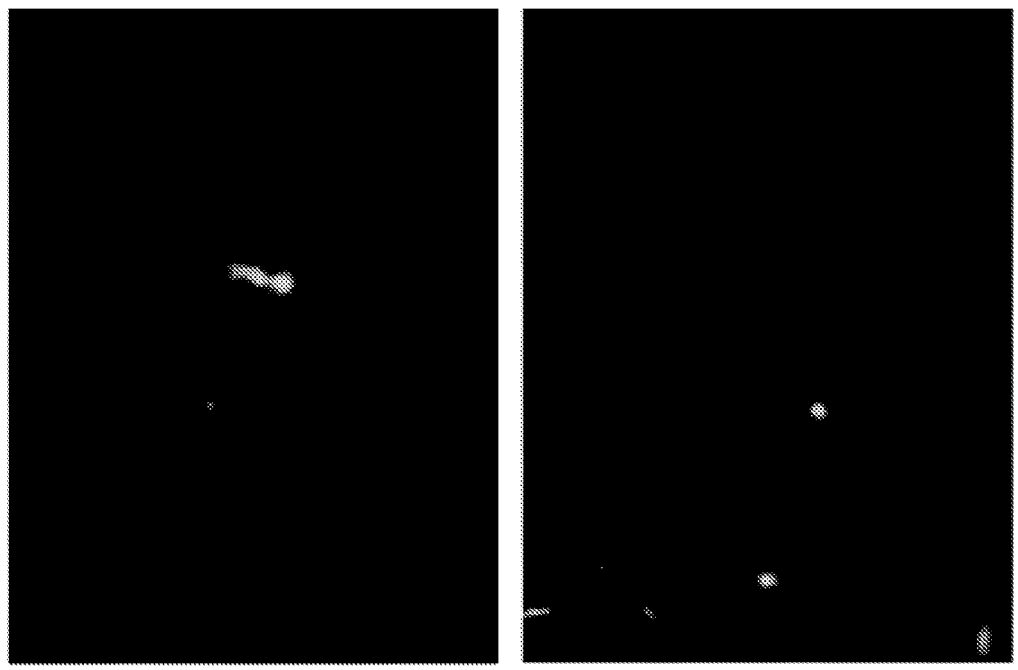
FIGS. 17A & 17B are fluorescent images taken at 200× magnification of receiver/stimulators of the type illustrated in FIGS. 8 and 9 depicting bacteria attached in the region of the arcuate channel in the receiver unit.

The bright spots depicted in the fluorescent images indicate microbial colonization whereas the general glow as shown in FIGS. 14 and 15 for example, results from the low level fluorescence of the silicone material that forms the pocket and shell of the receiver/stimulator.

To obtain the enhanced surface smoothness for the silicone pocket 822 as exemplified by receiver/stimulator 800, the mold tool is designed to have no parts that are removed during production of the silicone shell 880, thereby preventing the degradation of the tool that would normally result from the small dents and blemishes formed in the tool during any part removal. Furthermore, the mold tools for silicone shell 880 are formed of unplated tool steel which is able to maintain an enhanced surface finish smoother than about 0.05 µm Ra.

Referring now to FIGS. 16A and 16B and 17A and 17B, there are shown fluorescent images taken at 200× magnification comparing the amount of attached bacteria in arcuate channels 25, 825 for receiver/stimulator 124 (FIGS. 16A and 16B) and receiver/stimulator 800 (FIGS. 17A and 17B) respectively for two sample devices of each type. As can be readily determined, arcuate channel 825 has less attached bacteria than the corresponding arcuate channel 25 of receiver/stimulator 124 where there are many attached bacteria including several small microcolonies (clumps).

Figure 18:
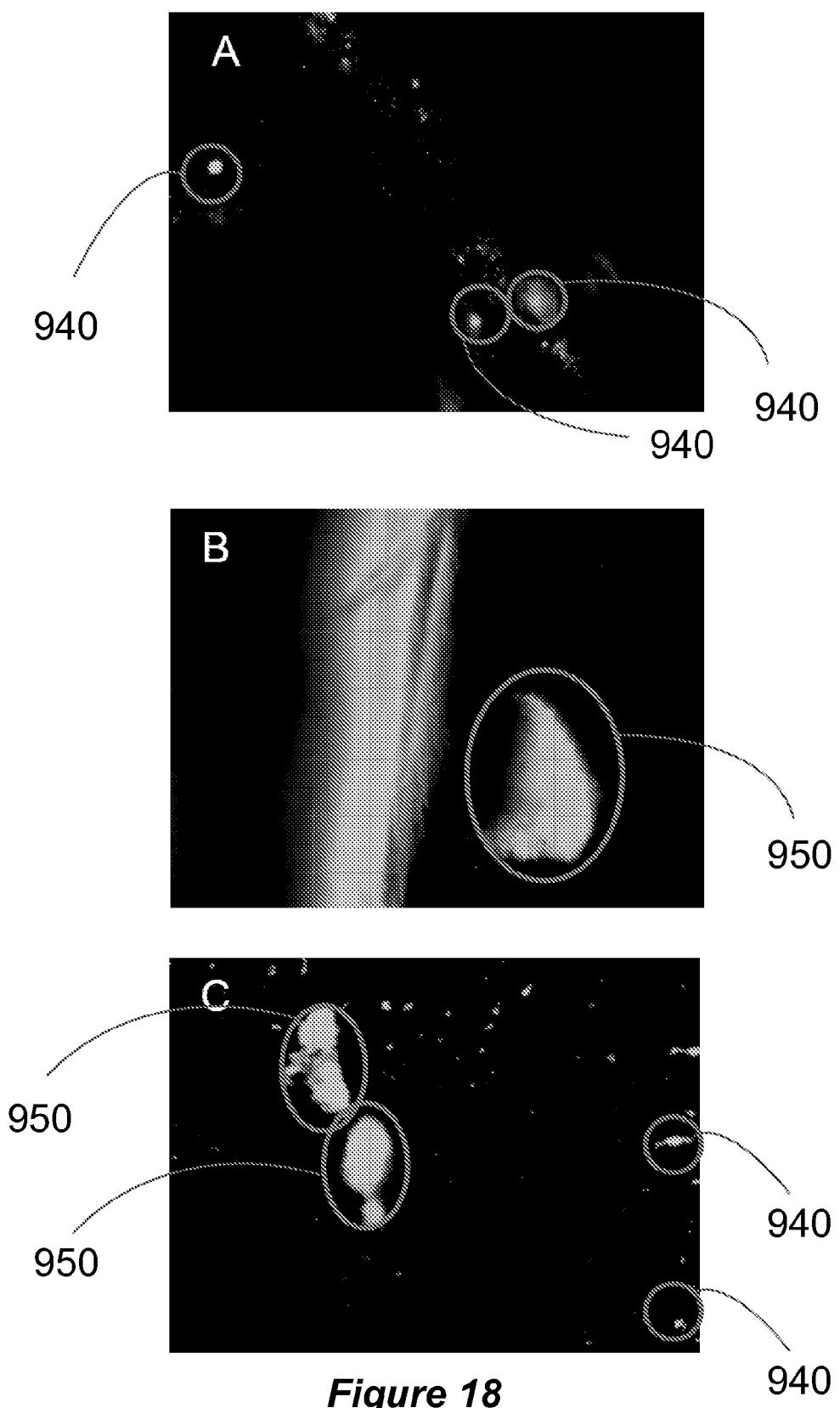
FIGS. 18A-18C is a series of fluorescent images taken at 200× magnification of a receiver/stimulator of the type illustrated in FIGS. 2 and 3 depicting bacteria attached to the skin or top side of stimulator unit.

Referring now to FIGS. 18A-18C and 19A and 19B, there are shown fluorescent images taken at 200× magnification comparing the amount of attached bacteria on the "skin" or "top" side of the stimulator unit 120, 820 for receiver/stimulator 124 (see FIGS. 18A-18C) and receiver/stimulator 800 (see FIG. 19A-19B) respectively. As shown in FIG. 18A, the raised lettering on ECE plate 29 of stimulator unit 120 provides an uneven surface that has large numbers of attached bacteria showing the initial stages of microcolony formation 940, especially in areas where the height changes results in grooves being formed in the surface of ECE plate 29. As shown in FIG. 18B, there is also significant attachment at the silicone edges around the lettering area where there is advanced microcolony formation 950.

Figure 19:
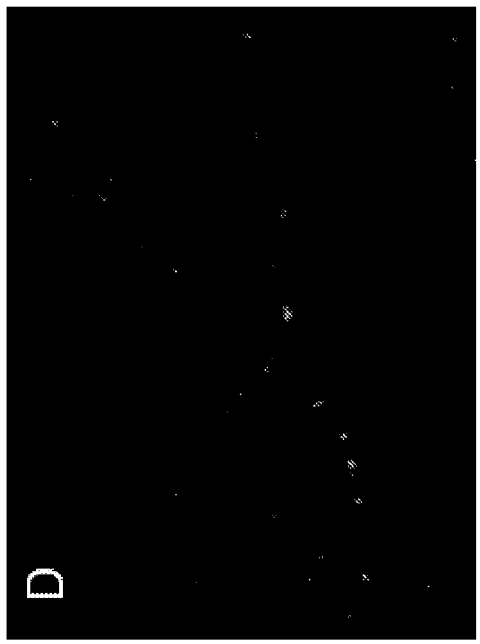
FIGS. 19A-19B is a series of fluorescent images taken at 200× magnification of a receiver/stimulator of the type illustrated in FIGS. 8 and 9 depicting bacteria attached to the skin or top side of stimulator unit.
Figure 19:

In comparison, and as shown in FIGS. 19A and 19B, for stimulator unit 820 of receiver/stimulator 800, where the same surface region is essentially flat with no features such as embossed lettering and a surface smoothness smoother than about 0.4 µm Ra, there is significantly reduced bacterial attachment and no microcolony formation.

While the experiment referred to above did not find significant differences in overall bacteria numbers with the average colony forming units (CFUs) for the two devices being 1.75 (±0.7)×106 CFUs for receiver/stimulator 124 and 2.35 (±0.6)×106 CFUs for receiver/stimulator 800, there is a clear decrease in bacterial attachment in previously identified problematic surface regions with the most pronounced difference between the devices being the substantial decrease in microcolony development.

Microcolony development comprising of approximately 50 or more cells that are attached to a surface region, was regularly observed on the stimulator unit 120 surface region of the receiver/stimulator 124 type devices whereas the receiver/stimulator 800 had only a few microcolonies on the equivalent stimulator unit 820 surface region. Furthermore, there were no microcolonies observed on the edges of the circular aperture 823 of the pocket 822 enclosing magnet 821 or in the arcuate channel 825 of receiver/stimulator 800 in contrast to these regions being the site of significant microcolony development in receiver/stimulator 124.

The significant reduction in the formation of microcolonies on a surface region as a result to adaptations to the surface form configuration in accordance with the present invention functions to reduce, including inhibit, the formation of a biofilm at these surface regions, thereby reducing the risk of a chronic infection arising and the resultant explant of an associated IMD.

While in the experimental testing reported and discussed in the specification the efficacy of the present invention has been demonstrated using the bacteria *Staphylococcus aureus*, and some embodiments of the invention will be applicable to other types of microbe that may be present on an IMD including but not limited to bacteria such as *Staphylococcus epidermidis, Pseudomonas aeruginosa, Serratia marcescens, Enterococcus faecalis, Escherichia coli, Haemophilus influenzae, Streptococcus viridans* and fungi such as *Candida albicans* and *Fusarium oxysporum*.

In accordance with an exemplary embodiment of the present invention, an implantable medical device (IMD) may be formed by adapting the surface form configuration of a surface region of the IMD to reduce, including inhibit, formation of a biofilm by applying one or more of the following non exhaustive list of design methodologies: Adapting the surface form configuration of the surface region by reducing the overall surface curvature. In one exemplary illustrative embodiment this may include increasing the aspect ratio of a depression or channel located on the surface region where as referred to earlier the aspect ratio is defined as the ratio of the width of the depression or channel and the depth of the depression or channel. In one exemplary embodiment the aspect ratio is to be not less than two.

In another illustrative exemplary embodiment, the surface curvature of a surface region is reduced by increasing the angle of an internal corner located on the surface region. This is achieved in one embodiment by ensuring that the angle of an internal corner is greater than 90 degrees or where appropriate greater than 135 degrees. Where the surface region includes an external curve then in another illustrative embodiment the radius of the external curve is increased and further where appropriate the radius of the external curve is ensured to be greater than half of the thickness of the implantable medical device corresponding to the surface region. An exemplary embodiment includes adapting the surface form configuration of a surface region by increasing the overall surface smoothness. In one illustrative exemplary embodiment, this is achieved by ensuring that the surface finish of the surface region is smoother than about 0.4 µm Ra.

A new model cochlear implant embodying design methodologies as referred to above and as depicted in FIGS. 8 and 9 has been released by the assignee of the current application and implanted into some 2200 recipients. At this stage there have been no reported infections and no explants due to infection. While at this point these results do not allow for a strict statistical comparison to be carried out between the new model and the older population of implants the results so far are indicative of the effectiveness of the design methodologies described herein in reducing the rate of infection associated with IMDs.

A first exemplary embodiment of present invention provides an implantable medical device (IMD) for implantation into a recipient, the IMD including at least one surface region, wherein the surface form configuration of the at least one surface region is adapted to in use reduce or inhibit formation of a biofilm on the at least one surface region.

An exemplary embodiment of the present invention relates to modifying an implantable medical device to reduce the risk of infection after implantation.

In another exemplary embodiment of the present invention, the surface form configuration of the at least one surface region is adapted to inhibit or reduce the attachment of microbes or bacteria to the at least one surface region. In another exemplary embodiment of the present invention, the surface form configuration of the at least one surface region is adapted to reduce the overall surface curvature of the at least one surface region.

In another exemplary embodiment of the present invention, the overall surface curvature of the at least one surface region is reduced by increasing the aspect ratio of a depression or channel located on the at least one surface region, the aspect ratio defined as a ratio of the width of the depression or channel and the depth of the depression or channel.

In another exemplary embodiment of the present invention, increasing the aspect ratio of a depression or channel located on the at least one surface region includes ensuring that the aspect ratio is not less than two. In another exemplary embodiment of the present invention, the overall surface curvature of the at least one surface region is reduced by increasing the angle of an internal corner located on the at least one surface region. In another exemplary embodiment of the present invention, increasing the angle of an internal corner located on the at least one surface region includes ensuring that the angle of an internal corner is greater than 90 degrees.

In another exemplary embodiment of the present invention, the angle of an internal corner is greater than 135 degrees. In another exemplary embodiment of the present invention, the overall surface curvature of the at least one surface region is reduced by increasing the radius of an external curve located on the at least one surface region. In another exemplary embodiment of the present invention, increasing the radius of an external curve located on the at least one surface region includes ensuring that the radius is greater than half of a thickness of the implantable medical device corresponding to the at least one surface region.

In another exemplary embodiment of the present invention, the surface form configuration of the at least one surface region is adapted to increase the overall surface smoothness of the at least one surface region.

In another exemplary embodiment of the present invention, the overall surface smoothness is increased by ensuring that the surface finish of the at least one surface region is better than 0.4 µm Ra. In another exemplary embodiment of the present invention, the implantable medical device is a cochlear implant.

Another exemplary embodiment of the present invention provides a method of forming an implantable medical device (IMD), the method including adapting the surface form configuration of at least one surface region of the IMD to in use reduce or inhibit formation of a biofilm on the at least one surface region. In another exemplary embodiment of the present invention, the adapting of the surface form configuration of the at least one surface region is to inhibit or reduce the attachment of microbes or bacteria to the at least one surface region. In another exemplary embodiment of the present invention, the adapting of the surface form configuration of the at least one surface region includes reducing the overall surface curvature of the at least one surface region. In another exemplary embodiment of the present invention, the reducing of the overall surface curvature of the at least one surface region includes increasing the aspect ratio of a depression or channel located on the at least one surface region, the aspect ratio defined as a ratio of the width of the depression or channel and the depth of the depression or channel. In another exemplary embodiment of the present invention, the increasing of the aspect ratio of a depression or channel located on the at least one surface region includes ensuring that the aspect ratio is not less than two.

In another exemplary embodiment of the present invention, the reducing of the overall surface curvature of the at least one surface region includes increasing the angle of an internal corner located on the at least one surface region. In another exemplary embodiment of the present invention, the increasing of the angle of an internal corner located on the at least one surface region includes ensuring that the angle of an internal corner is greater than 90 degrees. In another exemplary embodiment of the present invention, the angle of an internal corner is ensured to be greater than 135 degrees. In another exemplary embodiment of the present invention, the reducing of the overall surface curvature of the at least one surface region includes increasing the radius of an external curve located on the at least one surface region.

In another exemplary embodiment of the present invention, the increasing of the radius of an external curve located on the at least one surface region includes ensuring that the radius is greater than half of a thickness of the implantable medical device corresponding to the at least one surface region. In another exemplary embodiment of the present invention, the adapting of the surface form configuration of the at least one surface region includes increasing the overall surface smoothness of the at least one surface region. In another exemplary embodiment of the present invention, the increasing of the overall surface smoothness includes ensuring that the surface finish of the at least one surface region is better than 0.4 µm Ra. In another exemplary embodiment of the present invention, the implantable medical device formed in accordance with the second aspect of the invention is a cochlear implant.

It will be understood that the term "comprise" and any of its derivatives (eg. comprises, comprising) as used in this specification is to be taken to be inclusive of features to which it refers, and is not meant to exclude the presence of any additional features unless otherwise stated or implied.

The reference to any prior art in this specification is not, and should not be taken as, an acknowledgement of any form of suggestion that such prior art forms part of the common general knowledge.

Although illustrative embodiments of the present invention has been described in the foregoing detailed description, it will be understood that the invention is not limited to the embodiment disclosed, but is capable of numerous rearrangements, modifications and substitutions without departing from the scope of the invention as set forth and defined by the following claims.

The claims defining the invention are as follows:

1. An implantable medical device configured to be implanted in a recipient, comprising:
   an implantable case;
   a receiver unit electrically connected to one or more components in the implantable case; and
   a silicone shell configured to substantially encapsulate the case and the receiver unit, wherein one or more portions of an exterior surface of the silicone shell have a surface smoothness that is smoother than about 0.4 µm Ra to inhibit formation of a biofilm thereon after implantation in the recipient, and wherein the silicone shell comprises an arcuate depression adjacent to the receiver unit to provide flexibility to the receiver unit thereby permitting the receiver unit to flex about a contour of a skull of the recipient, and wherein a ratio of the width to depth of the arcuate depression is 2 or more at all locations of the arcuate depression.

2. The implantable medical device of claim 1, wherein one or more other portions of the exterior surface of the silicone shell have at least one of:
   an aspect ratio of about 2 or more;
   an angle of about 90 degrees or more; or
   a radius of curvature greater than about half a thickness of the implantable medical device, the thickness being on the same plane on which the radius of curvature is located.

3. The implantable medical device of claim 1, wherein the silicone shell encapsulating the case has an exterior length, a first exterior width, and an exterior thickness that is smaller than the exterior width, and wherein the silicone shell encapsulating the case has no angles less than 90 degrees.

4. The implantable medical device of claim 1, wherein the silicone shell encapsulating the case has an exterior length, an exterior width, and an exterior thickness that is smaller than the exterior width, wherein transitional regions extending from outer edges of a skin-side of the implantable medical device have an external radius of curvature greater than half the thickness, the thickness being on the same plane on which the external radius of curvature is located.

5. The implantable medical device of claim 4, wherein:
   the implantable medical device is a receiver-stimulator of a cochlear implant; and
   the implantable medical device is constructed and arranged to be implanted in the recipient such that the skin-side of the implantable medical device faces away from the skull of the recipient.

6. The implantable medical device of claim 1, wherein substantially the entire exterior surface of the silicone shell has a surface smoothness that is smoother than about 0.4 µm Ra.

7. The implantable medical device of claim 1, wherein one or more portions of the exterior surface of the silicone shell include an internal corner having an angle that is greater than 90 degrees.

8. The implantable medical device of claim 1, wherein one or more portions of the exterior surface of the silicone shell include an internal corner having an angle that is greater than 135 degrees.

9. The implantable medical device of claim 1, further comprising:
   a receptacle inflection region comprising an aperture containing a magnet.

10. The implantable medical device of claim 1, wherein a portion of the implantable case forms part of an exterior surface of the implantable medical device.

11. The implantable medical device of claim 10, wherein the portion of the implantable case that forms part of an exterior surface of the implantable medical device is an extra-cochlear electrode plate.

12. An implantable medical device configured to be implanted in a recipient, comprising:
- an implantable assembly including a silicone shell having an arcuate depression with an aspect ratio greater than 2 at all locations thereof, wherein the silicone shell comprises one or more portions with a surface smoothness that is smoother than about 0.4 μm Ra for inhibiting a formation of a biofilm thereon after implantation in the recipient, and wherein the silicone shell includes a plurality of exterior regions and wherein one or more the exterior regions of the shell have at least one of:
- an aspect ratio of about 2 or more;
- an angle of about 90 degrees or more; or
- a radius of curvature greater than about half a thickness of the implantable medical device, the thickness being located on the same plane on which the radius of curvature is located.

13. The implantable medical device of claim 12, wherein the arcuate depression is configured to provide flexibility to the silicone shell relative to the arcuate depression thereby permitting the shell to flex about a contour of a skull of the recipient.

14. The implantable medical device of claim 12, wherein the silicone shell includes a section encapsulating an implantable case, and wherein the section of the silicone shell encapsulating the implantable case includes an exterior length, an exterior width, and an exterior thickness that is smaller than the exterior width, and has no angles less than 90 degrees.

15. The implantable medical device of claim 14, the section of the silicone shell encapsulating the implantable case has no angles less than 135 degrees.

16. The implantable medical device of claim 12, wherein the silicone shell includes a section encapsulating an implantable case, and wherein the section of the silicone shell encapsulating the implantable case includes an exterior length, an exterior width, and an exterior thickness that is smaller than the exterior width,
- wherein transitional regions extending from outer edges of a skin-side of the implantable assembly have an external radius of curvature greater than half the thickness of the implantable medical device, the thickness being on the same plane on which the external radius of curvature is located.

17. The implantable medical device of claim 16, wherein:
- the implantable assembly is a receiver-stimulator of a cochlear implant; and
- the implantable assembly is constructed and arranged to be implanted in the recipient such that the skin side of the shell faces away from the skull of the recipient.

* * * * *